United States Patent
Reynolds

[11] Patent Number: 6,123,685
[45] Date of Patent: Sep. 26, 2000

[54] SYRINGE FOR INFUSION

[76] Inventor: David L. Reynolds, P.O. Box 600, 305 Knowiton Road, Lac Brome, Quebec, Canada, J0E 1V0

[21] Appl. No.: 08/917,128

[22] Filed: Aug. 25, 1997

Related U.S. Application Data

[63] Continuation of application No. 08/553,661, filed as application No. PCT/CA94/00277, May 16, 1994, abandoned.

[30] Foreign Application Priority Data

May 17, 1993 [GB] United Kingdom .................... 9310085

[51] Int. Cl.$^7$ .................................................. A61M 37/00
[52] U.S. Cl. ................................ 604/90; 604/88; 604/191
[58] Field of Search .................................. 604/70, 86, 90, 604/132, 141, 142, 143, 150, 191, 200, 217, 221, 222, 228, 201, 205, 88

[56] References Cited

U.S. PATENT DOCUMENTS

| | | |
|---|---|---|
| 2,605,765 | 8/1952 | Kollsman ............................... 604/135 |
| 3,965,898 | 6/1976 | Cloyd ..................................... 604/203 |
| 4,643,721 | 2/1987 | Brunet .................................... 604/191 |
| 4,973,308 | 11/1990 | Borras et al. ........................... 604/110 |
| 5,281,198 | 1/1994 | Haber et al. ....................... 604/191 X |

*Primary Examiner*—Wynn Wood Coggins
*Assistant Examiner*—A. T. Nguyen
*Attorney, Agent, or Firm*—Ridout & Maybee

[57] ABSTRACT

A syringe is modified to permit gradual administration of its contents with reduced problems due to seizing or stiction of its piston by dividing its piston axially into two parts, a front detached part and rear part which is the only part having provision for attachment to a syringe actuator. The rear part has a passage through which fluid can be gradually introduced from an actuator into a chamber between the parts so as to force the front part forward while the rear part is restrained against rearward movement. The passage may be initially closed by a septum which is penetrated by a cannula on the actuator. If the syringe actuator is a plunger, the syringe can be used conventionally.

11 Claims, 1 Drawing Sheet

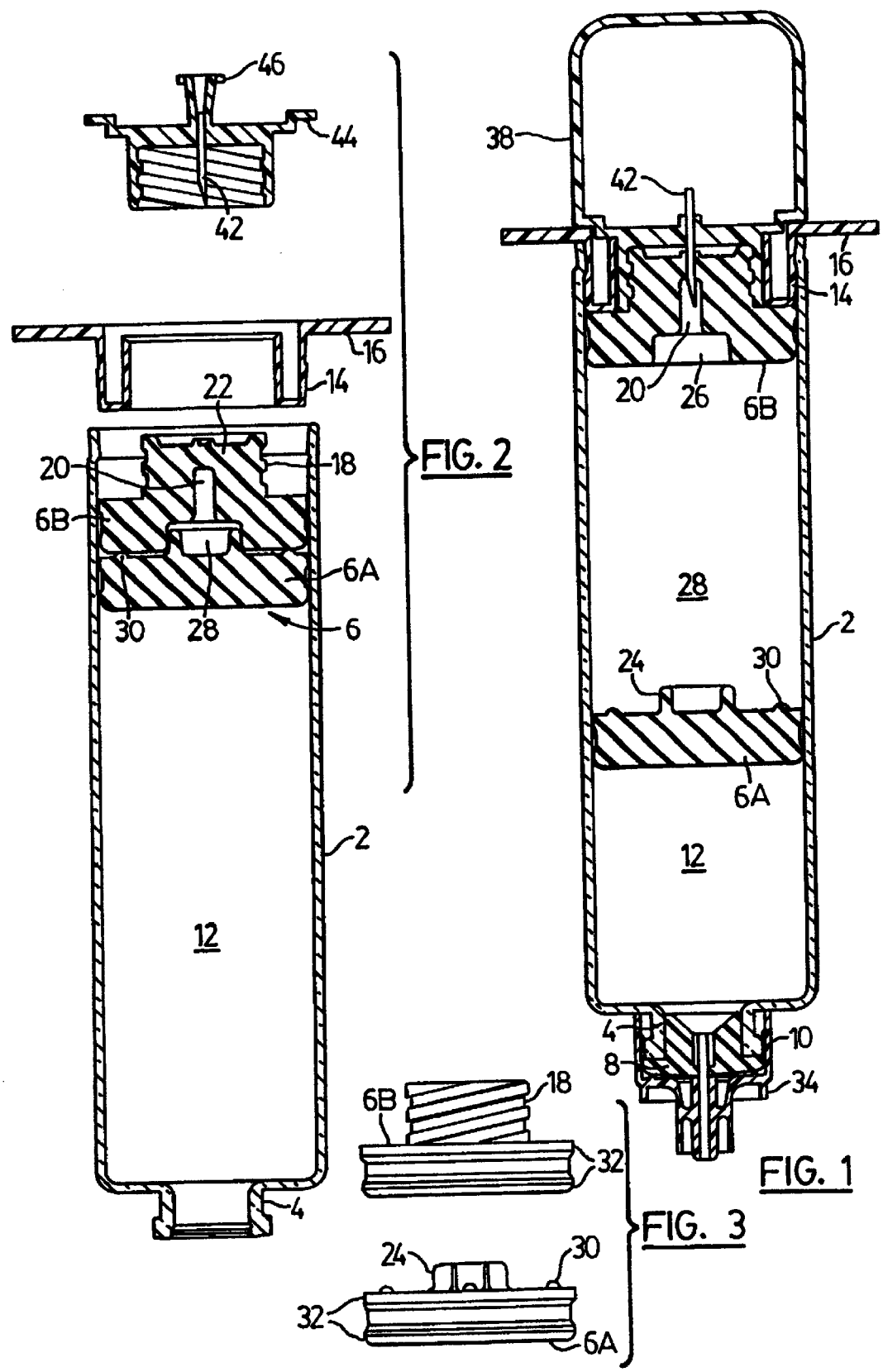

006,123,685

SYRINGE FOR INFUSION

This application is a continuation of application Ser. No. 08/553,661, filed Nov. 17, 1995, abandoned which is a 371 of PCT/CA94/00277 filed May 16, 1994.

This invention relates to syringes, particularly prefilled syringes, such as are utilized for the dispensing of pharmaceutical and personal care products.

In the context of this invention the term "syringe" is used broadly to refer to a container, having a tubular body usually of cylindrical cross-section, and liquid contents which are dispensed through a relatively small tubulation present or introduced at one otherwise closed end, hereinafter referred to as the forward end, of the body upon displacement of piston longitudinally within the body. By "prefilled" is meant either prefilled with a liquid which is dispensed, or prefilled with a liquid soluble or miscible component of such a liquid which can be reconstituted by addition of a second liquid diluent, solvent or carrier component immediately prior to use. The body of such a syringe is usually but not necessarily of glass or synthetic plastic material, and usually but not necessarily transparent.

It is important that the contents of a prefilled syringe be secure against leakage or contamination during storage, and in many cases during terminal sterilization which is required prior to storage. This entails that the piston makes a seal with the body which is hermetic or near hermetic. At least the peripheral walls of such pistons are usually formed of elastomeric material in compressive engagement, typically in plural longitudinally spaced annular zones, with an inside wall of the syringe body, in order to maintain the necessary seal. Despite various remedial measures which may be utilized, such as the use of silicone lubricants, this extensive engagement can give rise to significant problems when the time comes for the piston to be displaced.

There is sufficient frictional engagement between the piston and the wall of the body that substantial force may be required to move the piston, whilst "stiction" effects mean that the force required to initiate piston movement will usually be significantly greater than that required to maintain it. Since the piston will have some longitudinal resilience, stiction effects can make it very difficult to obtain smooth discharge of the contents of syringes at low rates. These problems are often aggravated by the tendency for the piston to "seize" during storage, with the material of the piston forming a more or less tenacious bond to the wall of the body. Such seizure may require considerable force to be applied to the piston to break the bond and permit initial movement of the piston.

When a plunger is utilized to activate the piston and expel the contents of a syringe at a fairly rapid rate, sufficient force can usually readily be applied to the piston through the plunger to overcome stiction or seizure provided that known remedial measures have been utilized, but difficulties arise when the contents of the syringe are to be dispensed slowly or in small quantities over a considerable period of time. When a pharmaceutical is to be infused slowly into a patient, available techniques include the use of syringe pumps, which incorporate an electric motor which slowly advanced the piston by means of a plunger, and IV bag and minibag systems in which the pharmaceutical is discharged from the syringe into a flexible bag of fluid and is thence infused into the patient at a controlled rate. Syringe pumps are expensive and cannot always prevent irregularities of discharge due to stiction effects, particularly at very low discharge rates. Bag based systems cannot readily be set up to provide very low discharge rates and require an extra stage of preparation as well as more dilution of the pharmaceutical than may be appropriate in some cases.

It has been proposed to provide syringes with two part pistons. In EP 03663338A, a mixing syringe utilizes pistons attached to a common plunger the front piston and the plunger having passageways which can be used in conjunction with a secondary plunger to provide a desired mixing action. In GB 2205750A, a two part piston, of which the front part is attached to a syringe plunger and has fluid non-return valves in its, is utilized to render a syringe non-refillable. In EP 0254765A, the plunger is again connected to the front part of the piston, with a space initially between the piston parts being evacuated through a one way valve in the plunger.

It is an object of the present invention to provide a syringe which addresses the problems discussed above and is better suited to applications in which the syringe contents are to be discharged at a low rate or in small quantities, whilst maintaining normal functionality. While it uses a two part piston, it does so in a manner quite different from the prior art discussed above.

According to the invention, a syringe has a piston which is formed in two separate but normally abutting parts in longitudinal tandem within and in sealing relationship with a syringe body, namely a detached imperforate front part nearer the forward end of the body and preferably of relative smaller axial extent, and a rear part preferably of relatively greater axial extent, and formed with passageway means, which may be initially obturated, for establishing fluid communication between rear and front surfaces of that part. Only the rear part of the piston has provision for mechanical connection to a syringe actuator. A retainer ring is engaged with a rear end of the syringe body to restrain the rear part of the piston against expulsion from the syringe body. A rear surface of the front part normally abuts and is supported by a front surface of the rear part, and the two parts cooperate to provide a high degree of sealing between the piston and the body. The provision for mechanical connection to a syringe actuator provides both for connection to a mechanical actuator, and for connection with a fluid pressure actuator communicable with the passageway. By passing fluid through the passageway, from the rear to the front of the rear part, into a chamber between the two parts, the front part may be displaced forwardly relative to the rear part, thus in turn applying pressure to the syringe contents to expel the latter, but the frictional engagement between the front part and the wall of the body will be much reduced as compared with the piston as a whole, since the degree of engagement of the front part with the wall is reduced compared with the piston as a whole. "Stiction" effects are also greatly reduced, as is the force required to overcome seizing, not only because of the reduced wall engagement, but because, for material of a given hardness, the transverse flexibility of the usually disc-like front part alone will be much increased as compared to a one piece piston. Any stiction or seizing will result in pressure behind the front portion bowing the latter forward, thus reducing its engagement with the body wall and overcoming the stiction or seizing. The overall effect is to greatly reduce the pressure needed to ensure displacement of the syringe contents, whilst at the same time attaining much smoother movement even at very low displacement rates. Rearward expulsion of the rear part of this piston is present by the retainer, and the rear part thus forms a reaction surface against which the fluid pressure may act to.

Further features of the invention are set forth in the appended claims, and will become apparent from the following description of an exemplary embodiment of the invention with reference to the accompanying drawings in which:

FIG. 1 is a longitudinal cross-sectional view of a syringe in accordance with the invention, during dispensing of the syringe contents by means of a gas-generator coupled to the syringe;

FIG. 2 is a similar but partially exploded view of components of a similar syringe prior to filling, together with an alternative cannula arrangement for applying fluid to operate the syringe;

FIG. 3 is a side elevational view of components of a piston of the syringe.

Referring to the drawings, the syringe is based on a "bottomless vial" constructed and filled generally as described in European Published Patent Application No. 0298585. It has a generally cylindrical glass (or synthetic plastic) body 2 having a narrower neck 4 at one front or top end, and an open bottom closed by an elastomeric piston 6. The body is filled with a pharmaceutical or personal care preparation through the neck 4, which is then closed by an elastomeric closure 8 and an annular cap 10, using conventional vial filling and capping machinery, although it should be understood that techniques utilized to fill the syringe with its contents 12 forms no part of the present invention. The piston 4 is retained within the syringe body by a retainer ring 14 which also provides a flange 16 providing a finger grip or reaction component enabling the syringe to be actuated in a conventional manner using a plunger attached to a screw threaded extension 18 formed at the back of the piston 6, either manually or by means of a syringe pump. The retainer ring is engaged with the syringe body in a manner somewhat similar to that described in WO 92/08507, but the details of the securement of the retainer ring do not form part of the present invention. The fitting of the ring 14 does however provide a support for the piston enabling the syringe to be terminally sterilized without danger of the piston being ejected by internal pressure developed within the body.

As compared to the pistons shown in the above-mentioned European patent application, the piston in the present embodiment is axially separated into two parts, a front part 6A nearer the forward end of the syringe body, and a rear part 6B. The rear part 6B is formed with an axially extending passage 20, which is initially closed at its rear end by a septum 22. A flange 24 on a rear surface of the portion 6A enters a recess 26 on a front surface of the portion 6B to enclose an initially small chamber 28, and pimples 30 on the rear surface of the portion 6A engage the front surface of the portion 6B. Both portions have annular ridges 32 on their outer periphery which engage the inside wall of the body 2.

In order to exploit the features of the invention, the chamber 28 is placed in communication with a source of fluid (gas or liquid) through the rear of the piston by penetrating the septum 22: in some cases, particularly where sterility is not at a premium, the septum may not be needed, or it may be replaced by some other means of obturating the passage. A pressure differential is set up as between this source of fluid and the pressure of the contents 12 of the syringe, which are placed in communication with a destination through a tubulation represented in this example by a connector cap 34 incorporating a cannula 36 which penetrates the closure 8. This connector may for example be coupled to a tube through which the content of the syringe is administered to a patient.

As pressure in the chamber 28 rises above the pressure in front of the portion 6A, a forward force will be applied to that portion. If there is any stiction or seizing to the wall of the body, the elasticity of the disc-shaped portion 6A will result in its bowing forward in the middle thus tending to release the ridges 32 from the body wall and providing some displacement of the syringe contents until the peripheral portions of the disc follow the centre portion.

If the syringe is raised above the level of discharge from the elastic end of the tube connected to the cap 34, a column of liquid in the tube will result in a negative pressure (relative to atmospheric) within the syringe body in front of the piston, and the mere rupture of the septum 22 to provide an air passage will result in the pressure in the chamber 28 rising above that within the body. Even quite a limited elevation of the syringe, comparable to that used in conventional IV administration, can be sufficient to result in smooth displacement of the piston portion 6A. The rate of displacement will depend on the capacity of the tube, and if microbore tube is used, a slow and controlled administration of the content of the syringe can be obtained over an extended period.

For many purposes a more positively controlled displacement will be desirable. One exemplary means of achieving this is to couple an electrochemical gas generator 38 of the type disclosed in U.S. Pat. No. 4,522,698 (Maget) to the rear portion 6B of the piston as shown in FIG. 1. The generator is switched on, and coupled by means of screw coupling 40 to the extension 18 so that a cannula 42 which forms the gas outlet of the device penetrates the septum 22 and communicates with the chamber 28. Electrochemical gas generators are commercially available which generate gas when activated at a very low and controlled rate so as to provide controlled displacement of the piston portion 6A. Rather than a gas generator, the unit 38 could be a compressed gas cartridge provided with a suitable pressure or flow rate regulator valve, or the cannula 42 could be secured in a threaded mounting 44 and provided with a coupling 46 for connection to a source of liquid such as water (which source need not be sterile) through appropriate flow or pressure regulating means. By storing such liquid used for displacement in a graduated container, an accurate indication may be provided thereby of quantity of liquid displaced from the syringe, without resorting to graduation of the syringe. In yet another variant, the syringe contents may be pumped from the syringe through the cannula 36, and the septum 22 is either absent, or ruptured by inserting a cannula 42 open to the atmosphere at its outer end, so that atmospheric pressure will move the piston portion 6A to compensate for liquid removed from the syringe without the necessity for admitting air into the syringe body ahead of the piston.

During storage, or conventional usage as a plunger operated syringe, the portion 6A is supported by the portion 6B to provide fully effective sealing of the syringe contents. The front portion 6A need only have sufficient axial extent to maintain its alignment in the body during displacement, and will usually have a lesser overall axial extent from the portion 6B. The passage 20 may be formed as part of the chamber 28, or in the rear surface of the portion 6B, or in any other way which permits fluid communication to be established readily between the front and rear surfaces of the portion 6B. The septum 22 or equivalent sealing structure will normally be desirable, but could in some cases be dispensed with or replaced by a removable or frangible seal over the rear end of the syringe body. Provided that at least the portion 6A of the piston is formed essentially of elastomeric material, the portion 6B could be formed of non-elastomeric material or be of composite construction. The pimples 30 limit contact between the piston parts so as to allow fluid pressure to be developed between them and avoid the risk of unwanted adhesion between the parts. The pimples or equivalent protuberances could of course be formed on either or both parts.

What is claimed is:

1. A syringe comprising a syringe body, a piston (6) which is formed in two separate parts in longitudinal tandem within the syringe body (2), wherein the piston parts are a detached imperforate front part (6A) formed essentially of elastomeric material and nearer a forward end of the syringe body, and a normally abutting rear part (6B) defining a passageway for establishing communication between rear and front surfaces of that rear part, only the rear part having at its rear surface, surrounding the passageway, a connector (18) for connection of a syringe actuator when the syringe is used, wherein a retainer is engaged with a rear end of the syringe body to restrain the rear part (6B) against expulsion from the syringe body, said retainer defining an opening through which said connector is accessible to an actuator, and wherein the connector is configured to provide a fluid connection between said passage in said rear part and a pressurized fluid source in an actuator, and a mechanical coupling between said rear part and an actuator, whereby by selection of a suitable actuator, said connector provides one of means for mechanically actuating the syringe by application of mechanical pressure to the rear piston part, and means for fluid actuation of the syringe by allowing fluid to be introduced between said piston parts through said passageway.

2. A syringe according to claim 1, wherein the piston parts (6A, 6B) cooperate to form a chamber (28) between said parts with which said passageway (20) communicates.

3. A syringe according to claim 1, wherein the front part (6A) of the piston is of generally disc-shaped configurations, and thin enough to bow under the application of differential fluid pressures to front and rear surfaces thereof.

4. A syringe according to claim 1, wherein the front part (6A) of the piston is of lesser axial extent than the rear part (6B).

5. A syringe according to claim 1, wherein at least one of the piston parts is formed with protuberance (30) to limit contact with the other part.

6. A syringe according to claim 1, wherein the passageway is closed by a perforable septum (22).

7. A method of discharging contents of syringe, having a piston adapted for conventional actuation by a mechanical actuator, by use of a fluid pressure actuator, comprising forming a piston of the syringe in two separable but initially abutting parts, namely a detached imperforate front part formed essentially of elastomeric material, and a rear part formed with a passageway for establishing fluid communication between rear and front surfaces of said rear part, only the rear part having provision for mechanical connection to a syringe actuator, and actuating said piston by connecting said fluid pressure actuator to the rear part and introducing pressurized fluid through said passageway from said actuator while restraining said rear part against rearward motion.

8. A method according to claim 7, in which the front part of the piston is disk shaped and sufficiently flexible such that it will bow under pressure, and causing said front part to bow by the introduction of said pressurized fluid so as to overcome stiction effects.

9. A method according to claim 7, wherein the fluid pressure actuator is a gas generator.

10. A method according to claim 7, wherein the fluid pressure actuator is a coupling to a tube linked to a source of fluid pressure.

11. A method according to claim 7, wherein the step of coupling a fluid pressure actuator to the rear part includes penetration of a septum in the passageway by a cannula on the fluid pressure.

* * * * *